United States Patent [19]

Helbig et al.

[11] 4,405,596

[45] * Sep. 20, 1983

[54] PHARMACEUTICAL PREPARATIONS FOR AND TREATMENT PROCEDURES INVOLVING INCREASING PLASMA BICARBONATE LEVEL

[76] Inventors: Joachim W. Helbig, Traubinger Str.23, D-1832 Tutzing; Klaus F. Kopp, Aschlkofener Str. 4, D-8017 Ebersberg, both of Fed. Rep. of Germany

[*] Notice: The portion of the term of this patent subsequent to Sep. 15, 1998, has been disclaimed.

[21] Appl. No.: 302,628

[22] Filed: Sep. 15, 1981

Related U.S. Application Data

[63] Continuation-in-part of Ser. No. 85,066, Oct. 15, 1979, Pat. No. 4,289,750.

[51] Int. Cl.$^3$ .................... A61K 33/00; A61K 33/06; A61K 33/14
[52] U.S. Cl. ........................................ 424/33; 424/35; 424/81; 424/127; 424/153; 424/154; 424/317; 424/322
[58] Field of Search ................. 424/127, 81, 153, 154, 424/33, 35, 317, 322

[56] References Cited

U.S. PATENT DOCUMENTS

| | | | |
|---|---|---|---|
| 3,960,757 | 6/1976 | Morishita et al. | 252/316 |
| 3,968,277 | 7/1976 | Takase | 427/212 |
| 4,289,750 | 9/1981 | Kopp et al. | 424/33 |

FOREIGN PATENT DOCUMENTS 287292  9/1915  Fed. Rep. of Germany.

OTHER PUBLICATIONS

*Der Arzneimittelbrief,* 16(10), 89–94 (1982).
Richards, P., et al., *The Lancet,* 1972 (vol. 2), 994–997.
Barmatskii, V., et al., *Klin. Med.,* 56(7), 66–70 (1978).

*Primary Examiner*—Richard A. Schwartz
*Attorney, Agent, or Firm*—Browdy and Neimark

[57] ABSTRACT

The invention concerns a novel pharmaceutical preparation and methods of treatment associated therewith. More particularly, the invention is concerned with pharmaceutical preparations adapted to form or release resorbable bicarbonate ions only in the intestine of the subject. The oral dosage forms of the invention may comprise further active agents, and trace elements.

The dosage forms are for example useful in treating patients suffering from abnormal distribution or retention of body fluids or retention products, i.e. products which should be or which should desirably be cleared by kidney function.

22 Claims, No Drawings

PHARMACEUTICAL PREPARATIONS FOR AND TREATMENT PROCEDURES INVOLVING INCREASING PLASMA BICARBONATE LEVEL

This is a continuation-in-part of application Ser. No. 085,066 filed Oct. 15, 1979, now U.S. Pat. No. 4,289,750.

In said copending application, there is described and claimed a method of treating a subject suffering from abnormal distribution of body fluids and retention products which is as a result of altered renal function. The method comprises oral administration of an alkaline acting substance adapted to release sodium and bicarbonate ions in the small intestine of the subject. The substance is capable of increasing patient plasma bicarbonate level and the amount of substance administered, i.e. the therapeutically effective amount in the particular method of treatment described and claimed in said application, is sufficient to substantially correct metabolic acidosis and increase urine production and clearance of retention products.

Also disclosed and claimed in application Ser. No. 085,066, is an oral dosage form of an alkaline acting substance capable of increasing plasma bicarbonate level to a value in excess of that prior to treatment, which oral dosage form is for use in the method described above.

More specifically, it is described and claimed that this oral dosage form may comprise sodium bicarbonate enclosed within an acid-resistant alkali-decomposable enclosure. A variety of additional active agents such as may be employed in the therapy of diseases and ailments which can be as a result of partial or temporarily altered renal function are furthermore disclosed and claimed in relation to the method of treatment described above. One group of additional active agents disclosed and claimed are substances suitable for the prophylaxis and therapy of kidney stones, which substances are selected from the group consisting of an alkali or alkaline earth metal salt of citric acid, or urea. Another additional active agent is a calcium compound, such as calcium gluconate, suitable for supplementing calcium in a subject. Yet a further additional active agent is one suitable for supplementing potassium in a subject, such as one or more of potassium chloride potassium bicarbonate, and potassium citrate. The oral dosage form may additionally comprise trace elements recognised to contribute to the general well-being of patients.

There are also disclosed, but not specifically claimed, in application Ser. No. 085,066 uses for the oral dosage form of the alkaline acting substance discussed above.

It is one purpose of the present continuation-in-part application to specifically claim such uses, and also claim further subject matter comprised but not claimed in said application. Another purpose of the present continuation-in-part application is to disclose and claim additional subject matter not specifically disclosed in said application.

One use of the oral dosage form of an alkaline acting substance disclosed in said application Ser. No. 085,066 is that the occurence of acute renal failure (as defined below and also defined in said application) can be prevented by oral administration of an oral dosage form comprising the alkaline acting substance to a patient prior to surgery or other severe insults of the body which is likely to lead to risks to severe impediment of renal function or acute renal failure as defined. Procedures additional to surgery are administration of X-ray media, extreme exertion, cytotoxic drugs, intoxications, hypo- and hyperthermia, medical emergency conditions etc. The oral dosage form comprises an alkaline acting substance adapted to release sodium and bicarbonate ions and is capable of correcting at least in part conditions of metabolic acidosis which precede renal failure. The oral dosage form in this use may be adapted to release said sodium and bicarbonate ions in the small intestine of the patient. In other words, the oral dosage form employed in this use may be identical to the oral dosage form described and claimed in said application Ser. No. 085,066.

Acute renal failure as employed herein is defined as involving conditions of acidosis associated with rising creatinine and urea values in the patient plasma, urea concentration of less than 300 mg/dl in the urine, urine volume usually of less than 500 ml/24 hours, although polyuric acute renal failure may involve higher urine volumes, and urine pH of less than about 6. Additional aspects which can be observed are low inorganic phosphate and titratable acid levels in the urine and low urine osmolality.

In application Ser. No. 085,066 and herein, reference is consistently made to plasma in describing bicarbonate levels and other levels. It is now somewhat more modern or more accurate to refer to whole blood or simply blood rather than plasma when discussing concentrations of substances. In the interests of maintaining consistent terminology, plasma is referred to herein, it being understood that the term is not intended to exclude determinations made in blood. Thus, where plasma concentrations are referred to, these may be concentrations determined in whole blood.

Exemplary of patients who may be subjected to prophylactic administration of alkaline acting substance to prevent acute renal failure are kidney transplant recipients and donors, or patients with varying degrees of renal insufficiency, such as may be related to diabetes, age and pregnancy, who are to be subjected to surgery or severe insults of the body. The prophylactically effective amount should most preferably lead to a so-called "plasma base excess" being established. A consideration related to this preference is the fact that observations made in reversing of acute renal failure, namely to the point where polyuria sets in, have reflected a preliminary almost simultaneous increase in fresh patient urine pH value to about neutral or alkaline suggesting passage of excess bicarbonate.

Reference is made to application Ser. No. 085,066 to gain an understanding of what is intended by establishing a plasma base excess.

Other uses of the oral dosage form of an alkaline acting substance disclosed in said application Ser. No. 085,066 is administration thereof immediately following severe intoxications, administration to elderly patients (who might also be suffering from incomplete renal function) exhibiting such conditions as dropsy, peripheral edemas, varicose veins and like disturbances. In many cases, such patients have responded extraordinarily well to treatment with the novel pharmaceutical preparation of the present invention. Another disclosure is that bicarbonate-induced alkalotic volume contraction may have the effect of lowering elevated blood pressure.

Further, it is disclosed that various conditions of edema have been observed to be aleviated. There is also mention of treatment of a variety of ailments reflected by abnormal distribution and retention of body fluids, for example as may occur in old age, pregnancy and dietary indiscretion. An observation made is that the invention also comprises prophylactic approaches and that one which is worthy of mention is prevention of the formation of kidney stones. Such prophylactic action may be encouraged by inclusion in oral preparations of substances such as alkali or alkaline earth metal citrates, or inclusion of urea itself. Thus, where increased urine volume may be encouraged by elevated plasma bicarbonate levels, presence of increased amounts of citrate or urea in the urine volume can decrease tendencies of kidney stone formation.

In like manner, presence of increased amounts of citrate or urea in increased urine volumes can regularly be successfully employed to assist in the elimination of kidney stone fines and kidney stones.

For purposes of maintaining a general state of well-being, particularly in elderly patients, trace elements today recognised to contribute to such may be included in oral preparations.

Also disclosed is that oral preparations of the invention are highly effective in increasing urine volume when administered at correct minimum dosage levels as described and have been found to exercise extraordinarily beneficial effects in the therapy of a multitude of body fluid distribution and fluid retention disorders.

Uses of oral pharmaceutical preparation of the invention are stated more specifically or more completely as follows:

(A) Treatment of edema or other forms of fluid overload, e.g.
  (a) edema or fluid overload during pregnancy
  (b) edema of hepatic origin, cardiac edema, nephrogenic edema, hypostatic edema, allergic edema, edema of hormonal origin, edema of premenstrual origin, edema in conjunction with contraceptives, traumatic edema, post-operative edema, injuries.

(B) Protection from nephrotoxic substances or other substances known to lead to altered renal function, e.g.
  (a) cytotoxic drugs (anti-cancer drugs)
  (b) antibiotics
  (c) analgetics
  (d) antiflammatories
  (e) others (C) Increasing urine volume, potentiating action on the effect of Diuretics, and protection of electrolytehomeostasis during diuretic treatment.

(D) Prophylactic conditioning of renal function of patients, particularly those suffering from one or other form of altered renal function, likely to develop severe impairment of renal function including renal failure following on procedures such as surgery or other severe insults of the body.

(E) Treatment of various forms of metabolic acidosis which involve a reduction of buffer content in plasma, e.g.
  (a) diabetes
  (b) gout, uricaemia
  (c) renal insufficiency
  (d) cardiac and pulmonary insufficiency
  (e) prolonged extreme exertion (F) Support and activation of kidney function.
  (a) with impaired kidney function, e.g. at the stage of preterminal renal insufficiency before blood dialysis is necessary
  (b) fluid retention at any stage of altered renal function, particularly at the beginning stages of uremia
  (c) regulation of electrolytehomeostasis arising from altered kidney function in old age and with renal disease in general (G) Acid-base disturbances of terminal renal failure, including patients on various modes of blood purification (dialysis, hemofiltration, peritoneal dialysis).

(H) Medical treatment procedures requiring increased amounts of fluid intake or administration of fluids.

(I) Treatment of side effects of laxative abuse.

(J) Dietary indiscretion or incorrect diet.
  (a) alcohol
  (b) insufficient intake of certain vegetables
  (c) excessive intake of protein
  (d) during fasting In all of the above situations, renal function is or will be altered in some or other fashion. Abnormal distribution or retention of body fluids, which will similarly in general be accompanied by abnormal distribution or retention of retention products, i.e. products which should be or which should desirably be cleared by kidney function, is the clinical condition common to the patients. Thus, proceeding in the above order, edema normally involves retention or inadequate clearance of sodium which in turn leads to retention of body fluids. The functioning of the kidney is thus altered or is lowered as compared to a situation in which sodium balance has not been disturbed by some or other factor. For example, edema during pregnancy will usually be of toxic or hormonal origin leading to sodium retention. Similar considerations apply to other types of edema which are also accompanied by sodium retention.

In the case of patients being subjected to treatment procedures with nephrotoxic substances, the kidney function is altered by virtue of the nephrotoxic action. The altered function leads to other disturbances.

The hypertensive patient is practically invariably being treated with a diuretic to increase renal excretion of sodium and hence lower retention of body fluids. The property of oral preparations of the present invention leading to increased urine volumes provides potential of lowering elevated blood pressure without altering renal function as is the result of the pharmaceutical action of diuretics. However, combined administration of oral preparations of the present invention with (reduced) dosages of diuretic may be advantageous to achieve adequate blood pressure lowering effects in the hypertensive patient.

Prophylactic conditioning of renal function is discussed in part above. However, it is noted here that experience gained in preventing acute renal failure, particularly in those suffering from altered renal function, strongly supports advantage in prophylactically conditioning renal function before the patient is subjected to treatment procedures which might affect kidney function. Desirably this conditioning procedure is initiated some several days before nephrotoxic type substances are administered. The patient should preferably achieve a maintained moderate state of alkalosis, also during therapy with the nephrotoxic substance, as reflected by a neutral to alkaline fresh urine pH value.

Metabolic acidosis is a result of altered renal function and is typical in diabetics, gout patients, renal insufficiency and temporarily after prolonged extreme exertion as with enduring sport. The kidney does not possess capability of excreting sufficient hydrogen ions and the patient to be treated would have a lowered plasma buffer content.

Support and activation of kidney function is a use of oral preparations of the present invention which is of some considerable importance. Clinical experience with oral preparations of the invention have shown that remaining kidney function can be optimised. Also, further deterioration of kidney function may in some cases be arrested or remaining kidney function may be extended over a prolonged period of time. Optimation of altered kidney function as in old age is of considerable benefit and the treatment procedures of this invention can often replace or at least supplement a variety of medications prescribed to older patients who are receiving medication directly or indirectly related to altered kidney function.

Terminal renal failure patients all suffer from acid-base balance disturbances. Administration of oral preparations of the present invention can advantageously be employed to correct these disturbances, for example between dialysis sessions.

Laxative abuse may in some cases lead to loss of basic substances with resulting metabolic acidosis, which can be corrected with the aid of oral preparations of the present invention. Dietary indiscretion of the nature described can also lead to metabolic acidosis, which can also be prevented or corrected with oral preparations of the invention. In some cases the condition may be of a temporary nature only, in which event the treatment procedure of the invention can also be temporary.

Disclosed, but not claimed independently of a method of treating a subject suffering from abnormal distribution of body fluids and retention products which is a result of altered renal function, is an oral dosage form of a pharmaceutically acceptable alkaline acting substance capable of increasing patient plasma bicarbonate level to a value in excess of that prior to treatment. In fact, the novel and essential characteristic of the oral dosage form of the invention is that resorbable bicarbonate ions are formed or released only in the intestine of a subject. This characteristic distinguishes the oral dosage form of the invention over other available oral preparations, administration of which can also lead to patient plasma bicarbonate level being increased to a value in excess of that prior to administration (treatment). Thus, in application Ser. No. 085,066, there is mention of oral administration of hexapotassium-hexasodium-pentacitrate-hydrate- or hexacalcium-hexasodium-heptacitrate-hydrate-complexes. Oral administration of these substances leaves much to be desired for reasons mentioned and in any case increases in plasma bicarbonate ion concentration which may be achieved by this administration proceeds via an entirely different mechanism involving cellular metabolism of citrate ions, notably by the liver. In contrast, oral preparations of the invention provide direct availability of the desired bicarbonate ions in the intestine of the subject, i.e. at resorption sites.

Clinical experience has shown that the oral preparation of the invention is extremely well accepted by patients undergoing treatment. Relative ease in achieving patient compliance has been experienced since patient condition (which condition is experienced by the patient) rapidly deteriorates if the patient does not ingest or does not ingest a sufficient amount of the preparation of the invention. Essentially, as discussed above and in application Ser. No. 085,066, a convenient means of monitoring adequate ingestion is by determining fresh urine pH value which should be maintained in the neutral to alkaline range. Experience resulting from lack of availability of the oral preparation of the invention and consequential needs to resort to citrate complex ingestion for purposes of increasing plasma bicarbonate level, showed poor response by patients and lack of compliance in view of unpalatability and side effects such as flatulence, nausea, vomiting and diarrhoea in some cases. With regard to the citrate complexes in general, it has also been observed that this is not an appropriate medication for correcting metabolic acidoses and maintaining an adequate acid-base and fluid balance over any extended period of time.

As indicated also in application Ser. No. 085,066, the oral dosage form of the invention, i.e. one which is adapted to form or release resorbable bicarbonate ions in the small intestine of a subject may be sodium bicarbonate enclosed within a gastric-juice-resistant alkali-decomposable enclosure. In other words the oral dosage form may in galenical terms be an enteric coated oral dosage form, in which the active agent comprises sodium bicarbonate. Cations other than sodium may be suitable in preparations of the invention but it is observed that sodium is in general preferred since the normal functioning of the kidney involves filtration and reabsorption of bicarbonate ions in the form of sodium bicarbonate. Sodium bicarbonate is in essence a physiological substance and is therefore preferred as the substance for forming or releasing resorbable bicarbonate ions in the intestine of a subject.

This oral dosage form, it is disclosed may comprise sodium bicarbonate enclosed within an acid resistant alkali decomposable enclosure, and a variety of additional active agents already mentioned above are disclosed. Additional active agents, not disclosed in application Ser. No. 085,066, which may be included in the oral dosage forms of the invention are aspartic acid or derivatives thereof. Thus, it is observed that aspartic acid or derivatives thereof comprised in asparagus, increase urine production. An aspartate specifically contemplated and which may be included in the oral dosage forms of the invention is magnesium aspartate or magnesium aspartate hydrochloride. This magnesium compound has also been found to lower uric acid values in patients receiving gout remedies. Exemplary unit dosage forms disclosed in application Ser. No. 085,066 to be convenient comprise from about 500 to about 1500 mg of alkaline acting substance, such as sodium bicarbonate. Unit dosage forms may be tablets, capsules or dragees enclosed by an acid-resistant (gastric-juice resistant) alkali-decomposable enclosure. In that the enclosure needs to be decomposable in the only moderately alkaline environment of the small intestine and in that the substance enclosed is also alkaline, or would be alkaline if liquid were to penetrate the coating prematurely, the preparation of the oral dosage forms of the invention is not without difficulty. However satisfactory results can be achieved with tablets, dragees and granulates coated with acrylic resins resistant to gastric juice, such as marketed by Röhm Pharma under the trademark "EUDRAGIT S". Similarly capsules comprising the alkali acting substance may be rendered resistant to gastric juice by treatment with a mixture of hydroxypropyl methyl cellulose phthalate and dibutyl phthalate. A variety of other coatings suitable for the indicated purpose may of course also be employed.

The pharmaceutical oral dosage forms of the invention are characterised by being substantially free of undesirable side effects known to exist for oral dosage forms of gastro-intestinal bicarbonate-releasing preparations. The active agent employed in the dosage forms of the invention essentially needs to be one which forms or releases or which has been adapted in the oral dosage form to form or release bicarbonate ions only in the intestine of a subject, without the possibility of reaction thereof with gastric secretions in the stomach of the subject. Additional to the specific oral dosage forms discussed above, it is noted that further oral dosage forms can be devised and are contemplated by the present invention.

The benefits of increasing plasma (or blood) bicarbonate level in accordance with procedures of the invention may for example be achieved with an active agent capable of forming or releasing bicarbonate ions following on reaction with intestinal secretions, such as following on reaction with enzymes present in intestinal secretions.

Enzymes are in general sensitive to pH and the active agent capable of forming or releasing bicarbonate ions may be protected from reaction with gastric secretions in the stomach of the subject by being associated with enzymes which are activated only in the environment of the intestine of a subject.

It has also been found that oral dosage forms of the invention, i.e. oral dosage forms adapted to form or release resorbable bicarbonate ions only in the intestine of a subject, may comprise a carbonate, such as sodium carbonate. Thus, provided that regions of over-alkalinity which can lead to irritation or damage of the walls of the small intestine can be avoided, carbonate ion release in the small intestine of a subject leads to form-action of two bicarbonate ions via reaction with water and reaction of liberated hydroxy ions with carbon dioxide available.

A variety of methods are available to avoid regions of over-alkalinity as a result of carbonate ion release. A procedure which is of relative theoretical simplicity but which requires careful control and specialised production techniques is to provide sustained slow release forms which release amounts of carbonate at a limited rate avoiding higher concentrations and enabling adequate distribution and opportunity for reaction to form bicarbonate ions. Another procedure which is more simply realised in practice is to limit higher concentrations of carbonate ions by including smaller amounts of carbonate by dilution with a substance which releases another anion which does not generate such alkalinity. In view of requirements for availability of relatively high bicarbonate amounts in many of the uses of the oral dosage forms of the present invention, the substance employed for releasing another anion is advantageously a bicarbonate. Thus, mixtures of a carbonate and a bicarbonate, with or without sustained release adaptions but necessarily adapted to release carbonate or bicarbonate ions in the intestine of a subject, provides a suitable source of bicarbonate ions which can be of some advantage over employment of bicarbonate alone in that amounts of carbonate and bicarbonate required to form or release a determined number of equivalents of bicarbonate ions would be lower than the amount of bicarbonate alone required to form or release the same determined number of equivalents of bicarbonate ions.

The relationship by weight of carbonate: bicarbonate in an oral dosage form of the invention comprising these two substances as bicarbonate releasing substances may be from 1:10 to 10:1. However, in order to avoid risks of alkalinity which is higher than acceptable to the walls of the small intestine, the amount of carbonate would in general be 50% by weight or less of the total amount of the substances for releasing bicarbonate ions comprised in the oral dosage forms of the invention.

Exemplary unit oral dosage forms of the present invention which comprise 50% by weight of sodium carbonate and 50% by weight of sodium bicarbonate as sodium and bicarbonate releasing substances, comprise a total of from about 230 mg to about 1000 mg of alkaline acting substance in order to achieve formation or release of about the same number of equivalents of bicarbonate ions as 500 to 1500 mg of sodium bicarbonate alone. Reductions in the amount of alkaline acting substance for releasing bicarbonate ions in the small intestine can be of some benefit since, as already mentioned, relatively large amounts of alkaline acting substance need to be administered in many of the uses and therapies for which the dosage forms of the present invention are intended.

Exemplary unit oral dosage forms of the invention suitable for treatment procedures of the invention may comprise the following constituents:

Core compositions (1) Bicarbonate forming or releasing substance: 200 to 1000 mg
(2) Adjuvants: 20 to 200 mg
(3) Potassium supplement: 0 to 100 mg
(4) Magnesium supplement: 0 to 500 mg
(5) Calcium supplement: 0 to 200 mg
(6) Further active agents: 0 to 200 mg
(7) Trace element components: 0 to 10 mg
(8) Colorants, carriers: 0 to 100 mg The core composition should possess a consistency enabling formation of a non-refractory tablet, dragee, granulate or capsule form. The form should also preferably be stable at temperatures well in excess of the temperature of warm-blooded animals, and preferably in excess of about 50° C. The formation of the dosage form should be effected in an environment of defined temperature and humidity conditions.

An exemplary coating composition suitable for coating a tablet form comprises the following essential constituents:

Cellulose acetate phthalate
Acrylic resin

An exemplary coating composition suitable for coating a capsule form to resist decomposition and reaction with gastric juices comprises the following essential constituents:

Gelatine
Hydroxymethylcellulose phthalate
Dibutyl phthalate.

Clinical evaluations have reflected that best results are achieved in the treatment of abnormal body fluid distribution such as result from altered renal function when the amount of alkaline acting substance administered is sufficient to create (and maintain) a moderate degree of metabolic alkalosis. Thus, as may be determined by blood gas analysis, bicarbonate concentrations in plasma should preferably lie above 24 mEq/l and most preferably above 26 mEq/l, which corresponds to about a 4 to 5 mEq/l base excess value.

Dosages which need to be applied to achieve values such as described above are of course dependent on the particular condition being treated. However, in general, it has been found that dosages ranging between 0.5 and 10 g/24 hours are adequate to establish preferred fresh patient urine pH value of above 6.5 and most preferably neutral to alkaline at a pH value between 6.8 and 8.

Indeed, most preferably, in view of indications reflected in the therapy of renal insufficiency, adequate renal function is regularly only established while fresh patient urine pH values are in the neutral to alkaline range.

We claim:

1. A pharmaceutical oral dosage form for use in treating altered renal function or prophylactically conditioning against such alterations of an active agent capable of forming or releasing bicarbonate ions and being for increasing plasma bicarbonate level of a subject to a value in excess of that prior to treatment, characterised in that said oral dosage form is substantially free of undesirable side effects known to exist for oral dosage forms of gastro-intestinal bicarbonate-releasing preparations, the active agent being one which forms or releases or which has been adapted in the oral dosage form to form or release resorbable bicarbonate ions only in the intestine of a subject without the possibility of reaction thereof with gastric secretions in the stomach of the subject.

2. A pharmaceutical oral dosage form according to claim 1, in which the active agent is one which forms or releases bicarbonate ions following reaction thereof with intestinal secretions.

3. A pharmaceutical oral dosage form according to claim 2, in which the active agent is one which forms or releases bicarbonate ions following reaction with enzymes present in intestinal secretions.

4. A pharmaceutical oral dosage form according to claim 1, in which the active agent has been adapted to form or release bicarbonate ions only in the intestine of the subject by being associated with an additional substance enabling the active agent to form or release bicarbonate ions only following reaction with intestinal secretions.

5. A pharmaceutical oral dosage form according to claim 4, in which said additional substance comprises enzymes which are activated only in the environment of the intestine.

6. A pharmaceutical oral dosage form according to claim 4, in which said additional substance comprises a gastric-secretion-resistant intestine-secretion-decomposable material.

7. A pharmaceutical oral dosage form according to claim 5, in which the active agent has been coated with said additional substance.

8. A pharmaceutical oral dosage form according to claim 7, in which the gastric-juice-resistant small-intestine-decomposable enclosure comprises a gastric-juice resistant acrylic resin.

9. A pharmaceutical oral dosage form according to claim 7, in which the gastric-juice resistant small-intestine-decomposable enclosure is a capsule enclosure rendered resistant to gastric juice with the aid of a mixture of gelatine hydroxypropyl methyl cellulose phthalate and dibutyl phthalate.

10. A pharmaceutical oral dosage form according to claim 7, in which the gastric-juice-resistant small-intestine-decomposable enclosure is a tablet coating rendered resistant to gastric juice with the aid of cellulose acetate phthalate and an acrylic resin.

11. A pharmaceutical preparation according to claim 1, in which the active agent is selected from the group consisting of a bicarbonate, a carbonate, or a mixture of a bicarbonate and a carbonate at a ratio by weight of from 1:10 to 10:1.

12. A pharmaceutical oral dosage form according to claim 1, in which the active agent is associated with a further active substance suitable for the prophylaxis and therapy of kidney stones, selected from the group consisting of an alkali metal or alkaline earth metal salt of citric acid, and urea.

13. A pharmaceutical oral dosage form according to claim 1, in which the active agent is associated with a calcium compound suitable for supplementing calcium in the subject.

14. A pharmaceutical oral dosage form according to claim 13, in which the calcium compound is calcium gluconate.

15. A pharmaceutical oral dosage form according to claim 1, in which the active agent is associated with a potassium compound suitable for supplementing potassium in the subject.

16. A pharmaceutical oral dosage form according to claim 15, in which the potassium compound is selected from the group consisting of potassium chloride, potassium bicarbonate, and potassium citrate.

17. A pharmaceutical oral dosage form according to claim 2, in unit dosage form, comprising from about 200 to about 1500 mg of a bicarbonate enclosed within a gastric-juice-resistant small-intestine-decomposable enclosure enabling release of bicarbonate ions only in the intestine of the subject.

18. A pharmaceutical oral dosage form according to claim 1, in which trace elements recognised to contribute to the general well-being of subjects are included in the oral dosage form.

19. A method of preventing severe impediment of renal function or acute renal failure, which comprises the step of orally administering to a patient likely to contract such severe impediment of renal function or renal failure, a prophylactically effective amount of the oral dosage form of claim 1.

20. A method according to claim 19, in which the prophylactically effective amount is sufficient to correct at least in part conditions of metabolic acidosis which precede severe impediment of renal function or acute renal failure.

21. A method according to claim 19, in which the prophylactically effective amount is sufficient to induce increased urine volume.

22. A method according to claim 19, in which the patient likely to contract severe impediment of renal function or renal failure is one suffering from altered renal function and which patient is to be subjected to a procedure likely to lead to severe impediment of renal function or acute renal failure in such patients.

* * * * *